United States Patent
Maas et al.

(10) Patent No.: US 7,060,852 B2
(45) Date of Patent: Jun. 13, 2006

(54) METHOD FOR PRODUCING ALKYL ARYL SULPHONATES

(75) Inventors: Heiko Maas, Mannheim (DE); Thomas Narbeshuber, Ibbenbueren (DE); Michael Roeper, Wachenheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/343,835

(22) PCT Filed: Aug. 10, 2001

(86) PCT No.: PCT/EP01/09297

§ 371 (c)(1),
(2), (4) Date: Feb. 10, 2003

(87) PCT Pub. No.: WO02/14266

PCT Pub. Date: Feb. 21, 2002

(65) Prior Publication Data

US 2004/0010161 A1  Jan. 15, 2004

(30) Foreign Application Priority Data

Aug. 11, 2000 (DE) .................. 100 39 995

(51) Int. Cl.
*C07C 309/31* (2006.01)
(52) U.S. Cl. .............. 562/94; 562/30; 562/45; 562/91; 562/93
(58) Field of Classification Search ........ 562/30, 562/45, 91, 93, 94; 585/502, 510, 511; 510/367, 510/392, 394, 400, 495
See application file for complete search history.

(56) References Cited

U.S. PATENT DOCUMENTS

| 3,351,654 A | * | 11/1967 | Gudelis | 562/94 |
| 3,409,637 A | * | 11/1968 | Ecccles et al. | 549/30 |
| 3,410,925 A | * | 11/1968 | Eby et al. | 585/511 |
| 3,442,964 A | | 5/1969 | Oldham | |
| 3,442,965 A | * | 5/1969 | Oldham | 585/455 |
| 4,959,491 A | * | 9/1990 | Threlkel | 562/94 |
| 4,962,249 A | * | 10/1990 | Chen et al. | 585/329 |
| 5,026,933 A | | 6/1991 | Blain et al. | |
| 5,057,638 A | * | 10/1991 | Sweeney | 585/324 |
| 5,344,997 A | * | 9/1994 | Kocal | 568/628 |
| 6,207,115 B1 | * | 3/2001 | Chodorge et al. | 422/134 |
| 6,281,181 B1 | * | 8/2001 | Vinson et al. | 510/235 |
| 6,580,009 B1 | * | 6/2003 | Schwab et al. | 585/324 |

FOREIGN PATENT DOCUMENTS

| WO | 88 07030 | 9/1988 |
| WO | 99 05241 | 2/1999 |
| WO | 99 07656 | 2/1999 |

OTHER PUBLICATIONS

English translation—International Preliminary Examination Report.
C. T. O'Connor and M. Kojima, "Alkene Oligomerization", CATALYSIS TODAY, vol. 6 (1990), pp. 329-349.
F. Niertich, "Intergrated tert. Butyl Alcohol/Dl-n-butenes Production from FCC $C_4$'S", PETROCHEMIE, 103, vol. 11, Nov. 1987, pp. 486-489.
Sanati et al, "The Oligomerization of Alkenes by Heterogeneous Catalysts", CATALYSIS, vol. 14, The Royal Society of Chemistry, 1999, pp. 236-287.

* cited by examiner

*Primary Examiner*—Rosalynd Keys
(74) *Attorney, Agent, or Firm*—Oblon, Spivak, McClelland, Maier & Neustadt, P.C.

(57) ABSTRACT

The invention relates to a process for the preparation of alkylarylsulfonates by
a) reaction of a $C_4$-olefin mixture over a metathesis catalyst for the preparation of an olefin mixture comprising 2-pentene and/or 3-hexene, and optional removal of 2-pentene and/or 3-hexene,
b) dimerization of the 2-pentene and/or 3-hexene obtained in stage a) over a dimerization catalyst to give a mixture containing $C_{10-12}$-olefins, and optional removal of the $C_{10-12}$-olefins,
c) reaction of the $C_{10-12}$-olefin mixtures obtained in stage b) with an aromatic hydrocarbon in the presence of an alkylating catalyst to form alkylaromatic compounds, where, prior to the reaction, additional linear olefins may be added,
d) sulfonation of the alkylaromatic compounds obtained in stage c), and neutralization to give alkylarylsulfonates, where, prior to the sulfonation, linear alkylbenzenes may additionally be added,
e) optional mixing of the alkylarylsulfonates obtained in stage d) with linear alkylarylsulfonates.

7 Claims, No Drawings

METHOD FOR PRODUCING ALKYL ARYL SULPHONATES

The present invention relates to a process for the preparation of alkylarylsulfonates, to alkylarylsulfonates obtainable by the process, and to alkylaryls obtainable in the process as intermediate, to the use of the alkylarylsulfonates as surfactants, preferably in detergents and cleaners, and to detergents and cleaners comprising these alkylarylsulfonates.

Alkylbenzenesulfonates (ABS) have been used for a long time as surfactants in detergents and cleaners. Following the use initially of surfactants based on tetrapropylene, which, however, had poor biodegradability, alkylbenzenesulfonates which are as linear as possible (LAS) have since been prepared and used. However, linear alkylbenzenesulfonates do not have adequate property profiles in all areas of application.

First, for example, it would be advantageous to improve their low-temperature washing properties or their properties in hard water. Likewise desirable is the ready ability to be formulated, derived from the viscosity of the sulfonates and their solubility. These improved properties are obtained by slightly branched compounds or mixtures of slightly branched compounds with linear compounds, although it is imperative to achieve the correct degree of branching and/or the correct degree of mixing. Too much branching adversely affects the biodegradability of the products. Products which are too linear have a negative effect on the viscosity and the solubility of the sulfonates.

Moreover, the proportion of terminal phenylalkanes (2-phenylalkanes and 3-phenylalkanes) relative to internal phenylalkanes (4-, 5-, 6- etc. phenylalkanes) plays a role for the product properties. A 2-phenyl fraction of about 30% and a 2- and 3-phenyl fraction of about 50% can be advantageous with regard to product quality (solubility, viscosity, washing properties).

Surfactants with very high 2- and 3-phenyl contents can have the considerable disadvantage that the processability of the products suffers as a result of a sharp increase in the viscosity of the sulfonates.

Moreover, the solubility behavior may not be optimum. Thus, for example, the Krafft point of a solution of LAS with very high or very low 2- or 3-phenyl fractions is up to 10–20° C. higher than in the case of the optimal choice of the 2- and 3-phenyl fraction.

The process according to the invention offers the essential advantage that, as a result of the combination of metathesis and dimerization, a unique olefin mixture is obtained which, following alkylation of an aromatic, sulfonation and neutralization, produces a surfactant notable for its combination of excellent application properties (solubility, viscosity, stability against water hardness, washing properties, biodegradability). With regard to the biodegradability of alkylarylsulfonates, compounds which are adsorbed less strongly to clarification sludge than traditional LAS are particularly advantageous.

For this reason, alkylbenzenesulfonates which are branched to a certain degree have been developed.

For example, U.S. Pat. No. 3,442,964 describes the dimerization of $C_{5-8}$-hydrocarbons in the presence of a cracking catalyst coated with a transition metal, giving predominantly olefins having two or more branches. These olefins are subsequently alkylated with benzene to give a nonlinear alkylbenzene. For example, a mixture of hexenes is dimerized over a silicon dioxide-aluminum oxide cracking catalyst and then alkylated using HF as catalyst.

WO 88/07030 relates to olefins, alkylbenzenes and alkylbenzenesulfonates which can be used in detergents and cleaners. In the process, propene is dimerized to give hexene, which in turn is dimerized to give largely linear dodecene isomers.

Benzene is then alkylated in the presence of aluminum halides and hydrofluoric acid.

U.S. Pat. No. 5,026,933 describes the dimerization of propene or butene to give monoolefins, where at least 20% of $C_{12}$-olefins which have a degree of branching of from 0.8 to 2.0 methyl groups/alkyl chain and have only methyl groups as branches. Aromatic hydrocarbons are alkylated over a shape-selective catalyst, preferably dealuminated MOR.

WO 99/05241 relates to cleaners which comprise branched alkylarylsulfonates as surfactants. The alkylarylsulfonates are obtained by dimerization of olefins to give vinylidine olefins, and subsequent alkylation of benzene over a shape-selective catalyst, such as MOR or BEA. This is followed by sulfonation.

The olefins hitherto used for the alkylation partly have too high or too low a degree of branching or do not produce an optimal ratio of terminal to internal phenylalkanes. Alternatively, they are prepared from costly starting materials, such as, for example, propene or alpha-olefins, and sometimes the proportion of the olefin fractions which is of interest for the preparation of surfactants is only about 20%. This leads to costly work-up steps.

The object of the present invention is to provide a process for the preparation of alkylarylsulfonates which are at least partially branched and thus have advantageous properties for use in detergents and cleaners compared with known compounds. In particular, they should have a suitable profile of properties of biodegradability, insensitivity toward water hardness, solubility and viscosity during the preparation and during use. In addition, the alkylarylsulfonates should be preparable in a cost-effective manner.

We have found that this object is achieved according to the invention by a process for the preparation of alkylarylsulfonates by a) reaction of a $C_4$-olefin mixture over a metathesis catalyst for the preparation of an olefin mixture comprising 2-pentene and/or 3-hexene, and optional removal of 2-pentene and/or 3-hexene, b) dimerization of the 2-pentene and/or 3-hexene obtained in stage a) over a dimerization catalyst to give a mixture containing $C_{10-12}$-olefins, and optional removal of the $C_{10-12}$-olefins, c) reaction of the $C_{10-12}$-olefin mixtures obtained in stage b) with an aromatic hydrocarbon in the presence of alkylating catalyst to form alkylaromatic compounds, where, prior to the reaction, additional linear olefins may be added, d) sulfonation of the alkylaromatic compounds obtained in stage c), and neutralization to give alkylarylsulfonates, where, prior to the sulfonation, linear alkylbenzenes may additionally be added, e) optional mixing of the alkylarylsulfonates obtained in stage d) with linear alkylarylsulfonates.

The combination of a metathesis of $C_4$-olefins with a subsequent dimerization and alkylation of aromatic hydrocarbons permits the use of cost-effective starting materials and of preparation processes which make the desired products accessible in high yields.

According to the invention, it has been found that the metathesis of $C_4$-olefins produces products which can be dimerized to give slightly branched $C_{10-12}$-olefin mixtures.

These mixtures can be used advantageously in the alkylation of aromatic hydrocarbons, giving products which, following sulfonation and neutralization, result in surfactants which have excellent properties, in particular with regard to the sensitivity toward hardness-forming ions, the solubility of the sulfonates, the viscosity of the sulfonates and their washing properties. Moreover, the present process is extremely cost-effective since the product streams can be designed flexibly such that no byproducts are produced. Starting from a $C_4$-stream, the metathesis according to the invention produces linear, internal olefins which are then converted into branched olefins via the dimerization step.

Stage a) of the process according to the invention is the reaction of a $C_4$-olefin mixture over a metathesis catalyst for the preparation of an olefin mixture comprising 2-pentene and/or 3-hexene, and optional removal of 2-pentene and/or 3-hexene. The metathesis can be carried out, for example, as described in WO 00/39058 or DE-A-100 13 253.

The olefin metathesis (disproportionation) is, in its simplest form, the reversible, metal-catalyzed transalkylidenation of olefins by rupture or reformation of C=C double bonds according to the following equation:

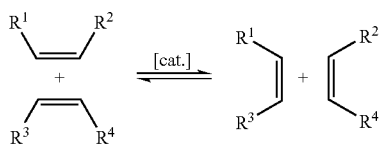

In the specific case of the metathesis of acyclic olefins, a distinction is made between self-metathesis in which an olefin is converted into a mixture of two olefins of differing molar masses (for example: propene→ethene+2-butene), and cross- or cometathesis, which is a reaction of two different olefins (propene+1-butene→ethene+2-pentene). If one of the reactants is ethene, this is generally referred to as ethenolysis.

Suitable metathesis catalysts are, in principle, homogeneous and heterogeneous transition metal compounds, in particular those of transition groups VI to VIII of the Periodic Table of the Elements, and homogeneous and heterogeneous catalyst systems in which these compounds are present.

Various metathesis processes starting from $C_4$ streams can be used according to the invention.

DE-A-199 32 060 relates to a process for the preparation of $C_5/C_6$-olefins by reaction of a feed stream which comprises 1-butene, 2-butene and isobutene to give a mixture of $C_{2-6}$-olefins. In this process, propene, in particular, is obtained from butenes. In addition, hexene and methylpentene are discharged as products. No ethene is added in the metathesis. If desired, ethene formed in the metathesis is returned to the reactor.

The preferred process for the preparation of optionally propene and hexene from a raffinate II feed stream comprising olefinic $C_4$-hydrocarbons comprises a) carrying out a metathesis reaction in the presence of a metathesis catalyst which comprises at least one compound of a metal of transition group VIb, VIIb or VIII of the Periodic Table of the Elements, in the course of which, butenes present in the feed stream are reacted with ethene to give a mixture comprising ethene, propene, butenes, 2-pentene, 3-hexene and butanes, where, based on the butenes, up to 0.6 mol equivalents of ethene may be used, b) first separating the product stream thus obtained by distillation into optionally a low-boiling fraction A comprising $C_2$–$C_3$-olefins, and into a high-boiling fraction comprising $C_4$–$C_6$-olefins and butanes, c) then separating the low-boiling fraction A optionally obtained from b) by distillation into a fraction comprising ethene and a fraction comprising propene, where the fraction comprising ethene is returned to the process step a), and the fraction comprising propene is discharged as product, d) then separating the high-boiling fraction obtained from b) by distillation into a low-boiling fraction B comprising butenes and butanes, an intermediate-boiling fraction C comprising 2-pentene, and a high-boiling fraction D comprising 3-hexene, e) where the fractions B and optionally C are completely or partly returned to the process step a), and the fraction D and optionally C are discharged as product.

The individual streams and fractions can comprise said compounds or consist thereof. In cases where they consist of the streams or compounds, the presence of relatively small amounts of other hydrocarbons is not ruled out.

In this process, in a single-stage reaction procedure, a fraction consisting of $C_4$-olefins, preferably n-butenes and butanes, is reacted in a metathesis reaction optionally with variable amounts of ethene over a homogeneous or, preferably, heterogeneous metathesis catalyst to give a product mixture of (inert) butanes, unreacted 1-butene, 2-butene, and the metathesis products ethene, propene, 2-pentene and 3-hexene. The desired products 2-pentene and/or 3-hexene are discharged, and the products which remain and unreacted compounds are completely or partly returned to the metathesis. They are preferably returned as completely as possible, with only small amounts being discharged in order to avoid accumulation. Ideally, there is no accumulation and all compounds apart from 3-hexene are returned to the metathesis.

According to the invention, up to 0.6, preferably up to 0.5, molar equivalents of ethene, based on the butenes in the $C_4$ feed stream, are used. Thus, only small amounts of ethene compared with the prior art are used.

If no additional ethene is introduced, only up to at most about 1.5%, based on the reaction products, of ethene form, which is recirculated, see DE-A-199 32 060. According to the invention, it is also possible to use larger amounts of ethene, the amounts used being significantly lower than in the known processes for the preparation of propene.

In addition, the maximum possible amounts of $C_4$ products and optionally $C_5$ products present in the reactor discharge are recirculated according to the invention. This applies in particular to the recirculation of unreacted 1-butene and 2-butene, and optionally of 2-pentene formed.

If small amounts of isobutene are still present in the $C_4$ feed stream, small amounts of branched hydrocarbons may also be formed.

The amount of branched $C_5$- and $C_6$-hydrocarbons which may additionally be formed in the metathesis product is dependent on the isobutene content in the $C_4$ feed and is preferably kept as low as possible (<3%).

In order to illustrate the process according to the invention in more detail in a plurality of variations, the reaction which takes place in the metathesis reactor is divided into three important individual reactions:

1. Cross-metathesis of 1-butene with 2-butene

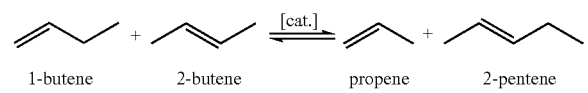

1-butene     2-butene     propene     2-pentene

2. Self-metathesis of 1-butene

1-butene     ethene     3-hexene

3. Optional Ethenolysis of 2-butene

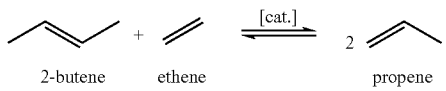

2-butene     ethene     propene

Depending on the respective demand for the target products propene and 3-hexene (the designation 3-hexene includes any isomers formed), and/or 2-pentene, the external mass balance of the process can be influenced in a targeted way by means of variable use of ethene and by shifting the equilibrium by recirculation of certain substreams. Thus, for example, the yield of 3-hexene is increased by suppressing the cross-metathesis of 1-butene with 2-butene by recirculation of 2-pentene to the metathesis step, so that no or extremely little 1-butene is consumed here. During the self-metathesis of 1-butene to 3-hexene, which then preferably proceeds, ethene is additionally formed, which reacts in a subsequent reaction with 2-butene to give the desired product propene.

Olefin mixtures which comprise 1-butene and 2-butene and optionally isobutene are obtained, inter alia, as $C_4$ fraction in various cracking processes, such as steam cracking or fluid catalytic cracking. As an alternative, it is possible to use butene mixtures as are produced during the dehydrogenation of butanes or by dimerization of ethene. Butanes present in the $C_4$ fraction have inert behavior. Dienes, alkynes or enynes are removed using customary methods such as extraction or selective hydrogenation prior to the metathesis step according to the present invention.

The butene content of the $C_4$ fraction used in the process is 1 to 100% by weight, preferably 60 to 90% by weight. The butene content is here based on 1-butene, 2-butene and isobutene.

Preference is given to using a $C_4$ fraction produced during steam cracking or fluid catalytic cracking or during the dehydrogenation of butane.

Here, the $C_4$ fraction used is preferably raffinate II, the $C_4$ stream being freed from undesirable impurities by appropriate treatment over adsorber guard beds, preferably over high-surface-area aluminum oxides or molecular sieves, prior to the metathesis reaction.

The low-boiling fraction A optionally obtained from step b), which comprises $C_2$–$C_3$-olefins, is separated by distillation into a fraction comprising ethene and a fraction comprising propene. The fraction comprising ethene is then recirculated to process step a), i.e. the metathesis, and the fraction comprising propene is discharged as product.

In step d, the separation into low-boiling fraction B, intermediate-boiling fraction C and high-boiling fraction D can, for example, be carried out in a dividing wall column. Here, the low-boiling fraction B is obtained at the top, the intermediate-boiling fraction C is obtained via a middle outlet and the high-boiling fraction D is obtained as bottoms.

In order to be able to better handle the differing amounts of products produced in the flexibly controlled process, it is, however, advantageous to carry out a two-stage separation of the high-boiling fraction obtained from b). Preferably, the high-boiling fraction obtained from b) is firstly separated by distillation into a low-boiling fraction B comprising butenes and butanes, and a high-boiling fraction comprising 2-pentene and 3-hexene. The high-boiling fraction is then separated by distillation into fractions C and D. The two embodiments are explained in more detail in FIGS. 1 and 2.

The metathesis reaction is here preferably carried out in the presence of heterogeneous metathesis catalysts which are not or only slightly isomerization-active and are selected from the class of transition metal compounds of metals of group VIb, VIIb or VIII of the Periodic Table of the Elements applied to inorganic supports.

The preferred metathesis catalyst used is rhenium oxide on a support, preferably on γ-aluminum oxide or on $Al_2O_3/B_2O_3/SiO_2$ mixed supports.

In particular, the catalyst used is $Re_2O_7/\gamma\text{-}Al_2O_3$ with a rhenium oxide content of from 1 to 20% by weight, preferably 3 to 15% by weight, particularly preferably 6 to 12% by weight.

The metathesis is, when carried out in a liquid phase, preferably carried out at a temperature of from 0 to 150° C., particularly preferably 20 to 80° C., and at a pressure of from 2 to 200 bar, particularly preferably 5 to 30 bar.

If the metathesis is carried out in the gas phase, the temperature is preferably 20 to 300° C., particularly preferably 50 to 200° C. The pressure in this case is preferably 1 to 20 bar, particularly preferably 1 to 5 bar.

The preparation of $C_5/C_6$-olefins and optionally propene from steam cracker or refinery $C_4$ streams may comprise the substeps (1) to (4):

(1) removal of butadiene and acetylenic compounds by optional extraction of butadiene with a butadiene-selective solvent and subsequently/or selective hydrogenation of butadienes and acetylenic impurities present in crude $C_4$ fraction to give a reaction product which comprises n-butenes and isobutene and essentially no butadienes and acetylenic compounds, (2) removal of isobutene by reaction of the reaction product obtained in the previous stage with an alcohol in the presence of an acidic catalyst to give an ether, removal of the ether and the alcohol, which can be carried out simultaneously with or after the etherification, to give a reaction product which comprises n-butenes and optionally oxygen-containing impurities, it being possible to discharge the ether formed or back-cleave it to obtain pure isobutene, and to follow the etherification step by a distillation step for the removal of isobutene, where, optionally, introduced $C_3$-, i-$C_4$- and $C_5$-hydrocarbons can also be removed by distillation during the work-up of the ether, or oligomerization or polymerization of isobutene from the reaction product obtained in the previous stage in the presence of an acidic catalyst whose acid strength is suitable for the selective removal of isobutene as oligoisobutene or polyisobutene, to give a stream containing 0 to 15% of residual isobutene, (3) removal of the oxygen-containing impurities from the product of the preceding steps over appropriately selected adsorber materials, (4) metathesis reaction of the resulting raffinate II stream as described.

The substep of selective hydrogenation of butadiene and acetylenic impurities present in crude $C_4$ fraction is preferably carried out in two stages by bringing the crude $C_4$ fraction in the liquid phase into contact with a catalyst which comprises at least one metal selected from the group consisting of nickel, palladium and platinum on a support, preferably palladium on aluminum oxide, at a temperature of from 20 to 200° C., a pressure of from 1 to 50 bar, a volume flow rate of from 0.5 to 30 m³ of fresh feed per m³ of catalyst per hour and a ratio of recycle to feed stream of from 0 to 30 with a molar ratio of hydrogen to diolefins of from 0.5 to 50, to give a reaction product in which, apart from isobutene, the n-butenes 1-butene and 2-butene are present in a molar ratio of from 2:1 to 1:10, preferably from 2:1 to 1:3, and essentially no diolefins and acetylenic compounds are present. For a maximum yield of hexene, 1-butene is preferably present in excess, and for a high protein yield, 2-butene is preferably present in excess. This means that the overall molar ratio in the first case can be 2:1 to 1:1 and in the second case 1:1 to 1:3.

The substep of butadiene extraction from crude $C_4$ fraction is preferably carried out using a butadiene-selective solvent selected from the class of polar-aprotic solvents, such as acetone, furfural, acetonitrile, dimethylacetamide, dimethylformamide and N-methylpyrrolidone, to give a reaction product in which, following subsequent selective hydrogenation/isomerization, the n-butenes 1-butene and 2-butene are present in a molar ratio 2:1 to 1:10, preferably from 2:1 to 1:3.

The substep of isobutene etherification is preferably carried out in a three-stage reactor cascade using methanol or isobutanol, preferably isobutanol, in the presence of an acidic ion exchanger, in which the stream to be etherified flows through flooded fixed-bed catalysts from top to bottom, the rector inlet temperature being 0 to 60° C., preferably 10 to 50° C., the outlet temperature being 25 to 85° C., preferably 35 to 75° C., the pressure being 2 to 50 bar, preferably 3 to 20 bar, and the ratio of isobutanol to isobutene being 0.8 to 2.0, preferably 1.0 to 1.5, and the overall conversion corresponding to the equilibrium conversion.

The substep of isobutene removal is preferably carried out by oligomerization or polymerization of isobutene starting from the reaction mixture obtained after the above-described stages of butadiene extraction and/or selective hydrogenation, in the presence of a catalyst selected from the class of homogeneous and heterogeneous Broensted or Lewis acids, see DE-A-100 13 253.

Selective Hydrogenation of Crude $C_4$ Fraction

Alkynes, alkynenes and alkadienes are undesired substances in many industrial syntheses owing to their tendency to polymerize or their pronounced tendency to form complexes with transition metals. They sometimes have a very strong adverse effect on the catalysts used in these reactions.

The $C_4$ stream of a steam cracker contains a high proportion of polyunsaturated compounds such as 1,3-butadiene, 1-butyne (ethylacetylene) and butenyne (vinylacetylene). Depending on the downstream processing present, the polyunsaturated compounds are either extracted (butadiene extraction) or are selectively hydrogenated. In the former case, the residual content of polyunsaturated compounds is typically 0.05 to 0.3% by weight, and in the latter case is typically 0.1 to 4.0% by weight. Since the residual amounts of polyunsaturated compounds likewise interfere in the further processing, a further concentration by selective hydrogenation to values <10 ppm is necessary. In order to obtain the highest possible proportion of the desired butenes, over-hydrogenation to butanes must be kept as low as possible.

Alternative: Extraction of Butadiene from Crude $C_4$ Fraction

The preferred method of isolating butadiene is based on the physical principle of extractive distillation. The addition of selective organic solvents lowers the volatility of specific components of a mixture, in this case butadiene. For this reason, these remain with the solvent in the bottom of the distillation column, while the accompanying substances which were not previously able to be separated off by distillation can be taken off at the top. Solvents used for the extractive distillation are mainly acetone, furfural, acetonitrile, dimethylacetaminde, dimethylformamide (DMF) and N-methylpyrrolidone (NMP). Extractive distillations are particularly suitable for butadiene-rich $C_4$ cracker fractions having a relatively high proportion of alkynes, including methylacetylene, ethylacetylene and vinylacetylene, and methylallene.

The simplified principle of solvent extraction from crude $C_4$ fraction can be described as follows: the completely vaporized $C_4$ fraction is fed to an extraction column at its lower end. The solvent (DMF, NMP) flows from the top in the opposite direction to the gas mixture and on its way downwards becomes laden with the more soluble butadiene and small amounts of butenes. At the lower end of the extraction column, part of the pure butadiene which has been isolated is fed in in order to drive out the butenes as far as possible. The butenes leave the separation column at the top. In a further column, referred to as a degasser, the butadiene is freed from the solvent by boiling out and is subsequently purified by distillation.

The reaction product from an extractive butadiene distillation is usually fed to the second stage of a selective hydrogenation in order to reduce the residual butadiene content to values of <10 ppm.

The $C_4$ stream remaining after butadiene has been separated off is referred to as $C_4$ raffinate or raffinate I and comprises mainly the components isobutene, 1-butene, 2-butenes, and n- and isobutanes.

Separating Off Isobutene from Raffinate I

In the further separation of the $C_4$ stream, isobutene is preferably isolated next since it differs from the other $C_4$ components by virtue of its branching and its higher reactivity. Apart from the possibility of a shape-selective molecular sieve separation, by means of which isobutene can be isolated in a purity of 99% and n-butenes and butane adsorbed on the molecular sieve pores can be desorbed again using a higher-boiling hydrocarbon this is carried out in the first instance by distillation using a so-called deisobutenizer, by means of which isobutene is separated off together with 1-butene and isobutene at the top, and 2-butenes and n-butane together with residual amounts of iso- and 1-butene remain in the bottoms, or extractively by reaction of isobutene with alcohols over acidic ion exchangers. Methanol (→MTBE) or isobutanol (IBTBE) are preferably used for this purpose.

The preparation of MTBE from methanol and isobutene is carried out at 30 to 100° C. and at a pressure slightly above atmospheric pressure in the liquid phase over acidic ion exchangers. The process is carried out either in two reactors or in a two-stage shaft reactor in order to achieve virtually complete isobutene conversion (>99%). The pressure-dependant azeotrope formation between methanol and MTBE requires a multistage pressure distillation to isolate pure MTBE, or is achieved by relatively new technology using methanol adsorption on adsorber resins. All other components of the $C_4$ fraction remain unchanged. Since small proportions of diolefins and acetylenes can shorten the life of the ion exchanger as a result of polymer formation, preference is given to using bifunctional PD-containing ion exchangers, in the case of which, in the presence of small amounts of hydrogen, only diolefins and acetylenes are hydrogenated. The etherification of the isobutene remains uninfluenced by this.

MTBE serves primarily to increase the octane number of gasoline. MTBE and IBTBE can alternatively be back-cleaved in the gas phase at 150 to 300° C. over acidic oxides to obtain pure isobutene.

A further possibility for separating off isobutene from raffinate I consists in the direct synthesis of oligo/poly-isobutene. In this way it is possible, over acidic homogeneous and heterogeneous catalysts, such as e.g. tungsten trioxide and titanium dioxide, and at isobutene conversions up to 95%, to obtain a product stream which has a residual isobutene content of a maximum of 5%.

Feed Purification of the Raffinate II Stream Over Adsorber Materials

To improve the operation life of catalysts used for the subsequent metathesis step, it is necessary, as described above, to use a feed purification (guard bed) for removing catalyst poisons, such as, for example, water, oxygen-containing compounds, sulfur or sulfur compounds or organic halides.

Processes for adsorption or adsorptive purification are described, for example, in W. Kast, Adsorption aus der Gasphase, VCH, Weinheim (1988). The use of zeolitic adsorbents is described in D. W. Breck, Zeolite Molecular Sieves, Wiley, New York (1974).

The removal of, specifically, acetaldehyde from $C_3$- to $C_{15}$-hydrocarbons in the liquid phase can be carried out as in EP-A-0 582 901.

Selective Hydrogenation of Crude $C_4$ Fraction

Butadiene (1,2- and 1,3-butadiene) and alkynes or alkenynes present in the $C_4$ fraction are firstly selectively hydrogenated in a two-stage process from the crude $C_4$ fraction originating from a steam cracker or a refinery. According to one embodiment, the $C_4$ stream originating from the refinery can also be fed directly to the second step of the selective hydrogenation.

The first step of the hydrogenation is preferably carried out over a catalyst which comprises 0.1 to 0.5% by weight of palladium on aluminum oxide as support. The reaction is carried out in the gas/liquid phase in a fixed bed (downflow mode) with a liquid cycle. The hydrogenation is carried out at a temperature in the range from to 80° C. and at a pressure of from 10 to 30 bar, a molar ratio of hydrogen to butadiene of from 10 to 50 and an LHSV of up to 15 $m^3$ of fresh feed per $m^3$ of catalyst per hour and a ratio of recycle to feed steam of from 5 to 20.

The second step of the hydrogenation is preferably carried out over a catalyst which comprises 0.1 to 0.5% by weight of palladium on aluminum oxide as support. The reaction is carried out in the gas/liquid phase over a fixed bed (downflow mode) with a liquid cycle. The hydrogenation is carried out at a temperature in the range from 50 to 90° C. and at a pressure from 10 to 30 bar, a molar ratio of hydrogen to butadiene of from 1.0 to 10 and an LHSV of from 5 to 20 $m^3$ of fresh feed per $m^3$ of catalyst per hour and a ratio of recycle to feed stream of from 0 to 15.

The resulting reaction product is referred to as raffinate I and, in addition to isobutene, has 1-butene and 2-butene in a molar ratio of from 2:1 to 1:10, preferably from 2:1 to 1:3.

Alternative: Separating Off Butadiene from Crude $C_4$ Fraction by Extraction

The extraction of butadiene from crude $C_4$ fraction is carried out using N-methylpyrrolidone.

According to one embodiment of the invention, the reaction product of the extraction is fed to the second stage of the selective hydrogenation described above in order to remove residual amounts of butadiene, the desired ratio of 1-butene to 2-butene being set in this selective hydrogenation step.

Separating Off Isobutene by Means of Etherification with Alcohols

In the etherification stage, isobutene is reacted with alcohols, preferably with isobutanol, over an acidic catalyst, preferably over an acidic ion exchanger, to give ethers, preferably isobutyl tert-butyl ether. According to one embodiment of the invention, the reaction is carried out in a three-stage reactor cascade, in which the reaction mixture flows through flooded fixed-bed catalysts from top to bottom. In the first reactor the inlet temperature is 0 to 60° C., preferably 10 to 50° C.; the outlet temperature is between 25 and 85° C., preferably between 35 and 75° C., and the pressure is 2 to 50 bar, preferably 3 to 20 bar. At a ratio of isobutanol to isobutene of from 0.8 to 2.0, preferably 1.0 to 1.5, the conversion is between 70 and 90%.

In the second reactor the inlet temperature is 0 to 60° C., preferably 10 to 50° C.; the outlet temperature is between 25 and 85° C., preferably between 35 and 75° C., and the pressure is 2 to 50 bar, preferably 3 to 20 bar. The overall conversion over the two stages increases to 85 to 99%, preferably 90 to 97%.

In the third and largest reactor, equilibrium conversion is achieved at equal inlet and outlet temperatures of from 0 to 60° C., preferably 10 to 50° C. The etherification and removal of the ether formed is followed by ether cleavage: the endothermic reaction is carried out over acidic catalysts, preferably over acidic heterogeneous catalysts, for example phosphoric acid on an $SiO_2$ support, at an inlet temperature of from 150 to 300° C., preferably at 200 to 250° C., and an outlet temperature of from 100 to 250° C., preferably at 130 to 220° C.

If an FCC $C_4$ fraction is used, it is to be expected that propane in amounts of around 1% by weight, isobutene in amounts of around 30 to 40% by weight, and $C_5$ hydrocarbons in amounts of around 3 to 10% by weight will be introduced, which may adversely affect the subsequent process sequence. The work-up of the ether accordingly provides the opportunity of separating off the components mentioned by distillation.

The resulting reaction product, referred to as raffinate II, has a residual isobutene content of from 0.1 to 3% by weight.

If larger amounts of isobutene are present in the product, for example when FCC $C_4$ fractions are used or when isobutene is separated off by acid-catalyzed polymerization to polyisobutene (partial conversion), the raffinate stream which remains can, according to one embodiment of the invention, be worked up by distillation prior to further processing.

Purification of the Raffinate II Stream Over Adsorber Materials

The raffinate II stream obtained after the etherification/polymerization (or distillation) is purified over at least one guard bed consisting of high surface-area aluminum oxides, silica gels, alumino-silicates or molecular sieves. The guard bed serves here to dry the $C_4$ stream and to remove substances which may act as catalyst poisons in the subsequent metathesis step. The preferred adsorber materials are Selexsorb CD and CDO and also 3 Å and NaX molecular sieves (13×). The purification is carried out in drying towers at temperatures and pressures which are chosen such that all components are present in the liquid phase. Optionally, the purification step is used to preheat the feed for the subsequent metathesis step.

The raffinate II stream which remains is virtually free from water, oxygen-containing compounds, organic chlorides and sulfur compounds.

When the etherification step is carried out with methanol for preparing MTBE, the formation of dimethyl ether as secondary component may make it necessary to combine two or more purification steps or to connect them in series.

Preferred metathesis catalysts are heterogeneous rhenium catalysts known from the literature, such as $ReO_7$ on $\gamma$-$Al_2O_3$ or on mixed supports, such as e.g. $SiO_2/Al_2O_3$, $B_2O_3/SiO_2/Al_2O_3$ or $Fe_2O_3/Al_2O_3$ having different metal contents. The rhenium oxide content is, regardless of the support chosen, between 1 and 20%, preferably between 3 and 10%.

The catalysts are used in freshly calcined form and require no further activation (e.g. by means of alkylating agents). Deactivated catalyst can be regenerated a number of times by burning off carbon residues at temperatures above 400° C. in a stream of air and cooling under an inert gas atmosphere.

A comparison of the heterogeneous catalysts shows that $Re_2O_7/Al_2O_3$ is active even under very mild reaction conditions (T=20 to 80° C.), while $MO_3/SiO_2$ (M=Mo, W) develops activity only at temperatures above 100 to 150° C. and, consequently, C=C double bond isomerization can occur as secondary reactions.

Mention may also be made of:
$WO_3/SiO_2$, prepared from $(C_5H_5)W(CO)_3Cl$ and $SiO_2$ in J. Mol. Catal. 1995, 95, 75–83;
3-component system consisting of $[Mo(NO)_2(OR)_2]_n$, $SnEt_4$ and $AlCl_3$ in J. Mol. Catal. 1991, 64, 171–178 and J. Mol. Catal 1989, 57, 207–220;
nitrodomolybdenum (VI) complexes from highly active precatalysts in J. Organomet. Chem. 1982, 229, $C_{19}$–$C_{23}$;
heterogeneous $SiO_2$-supported $MoO_3$ and $WO_3$ catalysts in J. Chem. Soc., Faraday Trans./1982, 78, 2583–2592;
supported Mo catalysts in J. Chem. Soc., Faraday Trans./1981, 77, 1763–1777;
active tungsten catalyst precursor in J. Am. Chem. Soc. 1980, 102(21), 6572–6574;
acetonitrile(pentacarbonyl)tungsten in J. Catal. 1975, 38, 482–484;
trichloro(nitrosyl)molybdenum(II) as catalyst precursor in Z. Chem. 1974, 14, 284–285;
$W(CO)_5PPH_3/EtAlCl_2$ in J. Catal. 1974, 34, 196–202;
$WCl_6$/n-BuLi in J. Catal 1973, 28, 300–303;
$WCl_6$/n-BuLi in J. Catal. 1972, 26, 455–458;
FR 2 726 563: $O_3ReO[Al(OR)(L)xO]nReO_3$ where R=$C_1$–$C_{40}$-hydrocarbon, n=1–10, x=0 or 1 and L=solvent,
EP-A-191 0 675, EP-A-129 0 474, BE 899897: catalyst systems comprising tungsten, 2-substituted phenoxide radicals and 4 other ligands, including a halogen, alkyl or carbene group,
FR 2 499 083: catalyst system comprising a tungsten, molybdenum or rhenium oxo transition metal complex with a Lewis acid,
U.S. Pat. No. 4,060,468: catalyst system comprising a tungsten salt, an oxygen-containing aromatic compound, e.g. 2,6-dichlorophenol and, if desired, molecular oxygen,
BE 776,564: catalyst system comprising a transition metal salt, an organometallic compound and an amine.

To improve the cycle time of the catalysts used, especially of the supported catalysts, it is advisable to purify the feed over adsorber beds (guard beds). The guard bed serves here to dry the $C_4$ stream and to remove substances which may act as catalyst poisons in the subsequent metathesis step. The preferred adsorber materials are Selexsorb CD and CDO and 3 Å and NaX molecular sieves (13×). The purification is carried out in drying towers at temperatures and pressures which are preferably chosen such that all of the components are present in the liquid phase. Optionally, the purification step is used for preheating the feed for the subsequent metathesis step. It may be advantageous to combine two or more purification steps with one another or to connect them in series.

Pressure and temperature in the metathesis step is chosen such that all reactants are present in the liquid phase (usually=0 to 150° C., preferably 20 to 80° C.; p=2 to 200 bar). Alternatively, it may, however, be advantageous, particularly in the case of feed streams having a relatively high isobutene content, to carry out the reaction in the gas phase and/or to use a catalyst which has lower acidity.

The reaction is generally complete after from 1 s to 1 h, preferably after 30 s to 30 min. It may be carried out continuously or batchwise in reactors such as pressurized-gas vessels, flow tubes or reactive distillation apparatuses, with preference being given to flow tubes.

Stage b)

In stage b), the 2-pentene and/or 3-hexene obtained in stage a) is dimerized over a dimerization catalyst to give a $C_{10-12}$-olefin mixture. The $C_{10-12}$-olefins obtained are optionally separated off.

During the dimerization of the olefins or olefin mixtures obtained in the metathesis step, dimerization products are obtained which, with regard to the further processing to give alkyl aromatics, have particularly favorable components and particularly advantageous compositions if a dimerization catalyst is used which contains at least one element from transition group VIII of the Periodic Table of the Elements, and the catalyst composition and the reaction conditions are chosen such that a dimer mixture is obtained which contains less than 10% by weight of compounds which have a structural element of the formula I (vinylidene group)

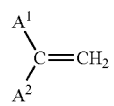

(I)

in which $A^1$ and $A^2$ are aliphatic hydrocarbon radicals.

For the dimerization, preference is given to using the internal, linear pentenes and hexenes present in the metathesis product. Particular preference is given to using 3-hexene.

The dimerization may be carried out with homogenous or heterogeneous catalysis. Preference is given to the heterogeneous procedure since here, firstly, catalyst removal is simplified and the process is thus more economical and, secondly, no environmentally harmful wastewaters are produced, as are usually formed during the removal of dissolved catalysts, for example by hydrolysis. A further advantage of the heterogeneous process is that the dimerization product does not contain halogens, in particular chlorine or fluorine. Homogeneously soluble catalysts generally contain halide-containing ligands, or they are used in combination with halogen-containing cocatalysts. Halogen may be incorporated from such catalyst systems into the dimerization products, which considerably impairs both the product quality and also the further processing.

For the heterogeneous catalysis, combinations of oxides of metals from transition group VIII with aluminum oxide on support materials of silicon oxides and titanium oxides, as are known, for example, from DE-A-43 39 713, are expediently used. The heterogeneous catalyst can be used in a fixed bed—then preferably in coarse form as 1 to 1.5 mm chips—or in suspended form (particle size 0.05 to 0.5 mm). The dimerization is, in the case of the heterogeneous procedure, expediently carried out at temperatures from 80 to 200° C., preferably from 100 to 180° C., under the pressure prevailing at the reaction temperature, optionally also under a protective gas at a pressure above atmospheric, in a closed system. To achieve optimal conversions, the reaction mixture is circulated a number of times, a certain proportion of the circulating product being continuously discharged and replaced with starting material.

The dimerization according to the invention produces mixtures of monounsaturated hydrocarbons, the components of which predominantly have a chain length twice that of the starting olefins.

Within the scope of the above details, the dimerization catalysts and the reaction conditions are preferably chosen such that at least 80% of the components of the dimerization mixture have one branch, or two branches on adjacent carbon atoms, in the range from ¼ to ¾, preferably from ⅓ to ⅔, of the chain length of their main chain.

A very characteristic feature of the olefin mixtures prepared according to the invention is their high proportion—generally greater than 75%, in particular greater than 80%—of components with branches, and the low proportion—generally below 25%, in particular below 20%—of unbranched olefins. A further characteristic is that, at the branching sites of the main chain, predominantly groups having (y−4) and (y−5) carbon atoms are bonded, where y is the number of carbon atoms of the monomer used for the dimerization. The value (y−5)=0 means that no side chain is present.

In the case of the $C_{12}$-olefin mixtures prepared according to the invention, the main chain preferably carries methyl or ethyl groups at the branching points.

The position of the methyl and ethyl groups on the main chain is likewise characteristic: in the case of mono-substitution, the methyl or ethyl groups are in the position P=(n/2)−m of the main chain, where n is the length of the main chain and m is the number of carbon atoms in the side groups, and in the case of disubstitution products, one substituent is in the position P and the other is on the adjacent carbon atom P+1. The proportions of monosubstitution products (single branching) in the olefin mixture prepared according to the invention are characteristically in total in the range from 40 to 75% by weight, and the proportions of double-branched components are in the range from 5 to 25% by weight.

The olefin mixtures obtainable by the above process (cf. WO 00/39058) are valuable intermediates particularly for the preparation, described below, of branched alkylaromatics for the preparation of surfactants.

Stage c)

In stage c), the $C_{10-12}$-olefin mixture obtained in stage b) is reacted with an aromatic hydrocarbon in the presence of an alkylation catalyst to form alkylaromatic compounds.

Here, preference is given to using an alkylation catalyst which leads to alkylaromatic compounds which have, in the alkyl radical, one to three carbon atoms with an H/C index of 1.

The alkylation can in principle be carried out in the presence of any alkylation catalysts.

Although $AlCl_3$ and HF can in principle be used, heterogeneous or shape-selective catalysts offer advantages. For reasons of plant safety and environmental protection, preference is nowadays given to solid catalysts, which include, for example, the fluorinated Si/Al catalyst used in the DETAL process, a number of shape-selective catalysts or supported metal oxide catalysts, and phyllosilicates and clays.

Regardless of the large influence of the feedstock used, in choosing the catalyst it is important to minimize compounds formed by the catalyst which are notable for the fact that they include in the alkyl radical carbon atoms with an H/C index of 0. Furthermore, compounds should be formed which, on average, have in the alkyl radical 1 to 3 carbon atoms with an H/C index of 1. This may, in particular, be achieved through the choice of suitable catalysts which, on the one hand, as a result of their geometry, suppress the formation of the undesired products but, on the other hand, permit an adequate rate of reaction.

The H/C index defines the number of protons per carbon atom in the alkyl radical.

Moreover, in choosing the catalysts, their tendency with regard to deactivation must be taken into consideration. One-dimensional pore systems in most cases have the disadvantage of rapid blocking of the pores as a result of degradation or formative products from the process. Catalysts with polydimensional pore systems are therefore to be preferred.

The catalysts used can be of natural or synthetic origin, the properties of which can be adjusted by methods known in the literature (e.g. ion exchange, steaming, blocking of acidic centers, washing out of extra lattice species, etc.) to a certain extent. It is important for the present invention that the catalysts at least in part have acidic character.

Depending on the type of application, the catalysts are either in the form of powders or in the form of moldings. The linkages of the matrices of the moldings ensure adequate mechanical stability, although free access by the molecules to the active constituents of the catalysts is to be ensured by sufficient porosity of the matrix. The preparation of such moldings is known in the literature and is detailed under the prior art.

Possible catalysts for the alkylation (nonexhaustive list) are: $AlCl_3$, $AlCl_3$/support (WO 96/26787), HF, $H_2SO_4$, ionic liquids (e.g. WO 98/50153), perfluorinated ion exchangers or NAFION/silica (e.g. WO 99/06145), F—Si/Al (U.S. Pat. No. 5,344,997) Beta (e.g. WO 98/09929, U.S. Pat. No. 5,877,370, U.S. Pat. No. 4,301,316, U.S. Pat. No. 4,301,317)

faujasite (CN 1169889), phyllosilicates, clays (EP 711600), fluorinated mordenite (WO 00/23405), mordenite (EP 466558), ZSM 12, ZSM-20, ZSM-38, mazzite, zeolite L, cancrinite, gmellinite, offretite, MCM-22, etc.

Preference is given to shape-selective 12-ring zeolites.

Preferred Reaction Method

The alkylation is carried out by allowing the aromatic compounds (the aromatic compound mixture) and the olefin (mixture) to react in a suitable reaction zone by bringing them into contact with the catalyst, working up the reaction mixture after the reaction and thus obtaining the desired products.

Suitable reaction zones are, for example, tubular reactors or stirred-tank reactors. If the catalyst is in solid form, then it can be used either as a slurry, as a fixed bed or as a fluidized bed.

Where a fixed-bed reactor is used, the reactants can be introduced either in cocurrent or in countercurrent. Realization as a catalytic distillation is also possible.

The reactants are either in the liquid and/or in the gaseous state.

The reaction temperature is chosen such that, on the one hand, as complete as possible a conversion of the olefin takes place and, on the other hand, the fewest possible by-products arise. The choice of temperature also depends decisively on the catalyst chosen. Reaction temperatures between 50° C. and 500° C. (preferably 80 to 350° C., particularly preferably 80–250° C.) can also be used.

The pressure of the reaction depends on the procedure chosen (reactor type) and is between 0.1 and 100 bar, and the space velocity (WHSV) is chosen between 0.1 and 100.

The reactants can optionally be diluted with inert substances. Inert substances are preferably paraffins.

The ratio of aromatic compound:olefin is usually set between 1:1 and 100:1 (preferably 2:1–20:1).

Aromatic Feed Substances

All aromatic hydrocarbons of the formula Ar—R are possible, where Ar is a monocyclic or bicyclic aromatic hydrocarbon radical, and R is chosen from H, $C_{1-5}$, preferably $C_{1-3}$-alkyl, OH, OR etc., preferably H or $C_{1-3}$-alkyl. Preference is given to benzene and toluene.

Stage d)

In stage d), the alkylaromatic compounds obtained in stage c) are sulfonated and neutralized to give alkylarylsulfonates.

The alkylaryls are converted into alkylarylsulfonates by
1) sulfonation (e.g. with $SO_3$, oleum, chlorosulfonic acid, etc., preferably with $SO_3$) and
2) neutralization (e.g. with Na, K, $NH_4$, Mg compounds, preferably with Na compounds).

Sulfonation and neutralization are adequately described in the literature and are carried out in accordance with the prior art. The sulfonation is preferably carried out in a falling-film reactor, but can also be carried out in a stirred-tank reactor. The sulfonation with $SO_3$ is to be preferred over the sulfonation with oleum.

Mixtures

The compounds prepared by processes described above are further processed (preferably) either as such, or are mixed beforehand with other alkylaryls and then passed to the further processing step. In order to simplify this process, it may also be sensible to mix the raw materials which are used for the preparation of the other alkylaryls mentioned above directly with the raw materials of the present process, and then to carry out the process according to the invention.

Thus, the mixing of slightly branched olefin streams from the process according to the invention with linear olefins, for example, is sensible. Mixtures of the alkylaryl-sulfonic acids or of the alkylarylsulfonates can also be used. The mixings are always undertaken with regard to optimization of the product quality of the surfactants prepared from the alkylaryl.

An exemplary overview of alkylation, sulfonation, neutralization is given, for example, in "Alkkylaryl-sulfonates: History, Manufacture, Analysis and Environmental Properties" in Surf. Sci. Ser. 56 (1996) Chapter 2, Marcel Dekker, New York, and references contained therein.

Stage e)

In stage e), the alkylarylsulfonates present in stage d) are additionally mixed with linear alkylaryl-sulfonates.

The invention also relates to alkylarylsulfonates obtainable by a process as described above.

The alkylarylsulfonates according to the invention are preferably used as surfactants, in particular in detergents and cleaners. The invention also relates to a detergent or cleaner comprising, in addition to customary ingredients, alkylarylsulfonates as described above.

Nonexhaustive examples of customary ingredients of detergents and cleaners according to the invention are listed below.

Bleach

Examples are alkali metal perborates or alkali metal carbonate perhydrates, in particular the sodium salts.

One example of an organic peracid which can be used is peracetic acid, which is preferably used in commercial textile washing or commercial cleaning.

Bleach or textile detergent compositions which can be used advantageously comprise $C_{1-12}$-percarboxylic acids, $C_{8-16}$-dipercarboxylic acids, imidopercarboxylic acids or aryldipercarboxylic acids. Preferred examples of acids which can be used are peracetic acid, linear or branched octane-, nonane-, decane- or dodecane-monoper-acids, decane- and dodecane-diperacid, mono- and diperphthalic acids, -isophthalic acids and -terephthalic acids, phthalimidopercaproic acid and terephthaloyldipercaproic acid. It is likewise possible to use polymeric peracids, for example those which contain the acrylic acid basic building blocks in which a peroxy function is present. The percarboxylic acids may be used as free acids or as salts of the acids, preferably alkali metal or alkaline earth metal salts.

Bleach Activator

Bleach catalysts are, for example, quaternized imines and sulfonimines, as described, for example, in U.S. Pat. No. 5,360,568, U.S. Pat. No. 5,360,569 and EP-A-0 453 003, and also manganese complexes as described, for example, in WO-A 94/21777. Further metal-containing bleach catalysts which may be used are described in EP-A-0 458 397, EP-A-0 458 398, EP-A-0 549 272.

Bleach activators are, for example, compounds from the classes of substance below:

polyacylated sugars or sugar derivatives having $C_{1-10}$-acyl radicals, preferably acetyl, propionyl, octanoyl, nonanoyl or benzoyl radicals, particularly preferably acetyl radicals, can be used as bleach activators. As sugars or sugar derivatives, it is possible to use mono- or disaccharides, and reduced or oxidized derivatives thereof, preferably glucose, mannose, fructose, sucrose, xylose of lactose. Particularly suitable bleach activators of this class of substance are, for example, pentacetylglucose, xylose tetraacetate, 1-benzoyl-2,3,4,6-tetraacetylglucose and 1-octanoyl-2,3,4,6-tetraacetylglucose.

A further class of substance which can be used comprises the acyloxybenzenesulfonic acids and alkali metal and alkaline earth metal salts thereof, it being possible to use $C_{1-14}$-acyl radicals. Preference is given to acetyl, propionyl, octanoyl, nonanoyl and benzoyl radicals, in particular acetyl radicals and nonanoyl radicals. Particularly suitable bleach activators from this class of substance are acetyloxybenzenesulfonic acid. They are preferably used in the form of their sodium salts.

It is also possible to use O-acyl oxime esters, such as, for example, O-acetylacetone oxime, O-benzoyl-acetone oxime, bis(propylamino) carbonate, bis(cyclo-hexylimino) carbonate. Examples of acylated oximes which can be used according to the invention are described, for example, in EP-A-0 028 432. Oxime esters which can be used according to the invention are described, for example, EP-A-0 267 046.

It is likewise possible to use N-acylcaprolactams, such as, for example, N-acetylcaprolactam, N-benzoylcapro-lactam, N-octanoylcaprolactam, carbonylbiscaprolactam.

It is also possible to use
- N-diacylated and N,N'-tetraacylated amines, e.g. N,N,N',N'-tetraacetylmethylenediamine and -ethylenediamine (TADE), N,N-diacetylaniline, N,N-diacetyl-p-toluidine or 1,3-diacylated hydantoins, such as 1,3-diactyl-5,5-dimethyl-hydantoin;
- N-alkyl-N-sulfonylcarboxamides, e.g. N-methyl-N-mesylacetamide or N-methyl-N-mesylbenzamide;
- N-acylated cyclic hydrazides, acylated triazoles or urazoles, e.g. monoacetylmaleic hydrazide;
- O,N,N-trisubstituted hydroxylamines, e.g. O-benzoyl-N,N-succinylhydroxylamine, O-acetyl-N,N-succinylhydroxylamine or O,N,N-triacetylhydroxyl-amine;
- N,N'-diacylsulfurylamides, e.g. N,N'-dimethyl-N,N'-diacetylsulfurylamide or N,N'-diethyl-N,N'-di-propionylsulfurylamide;
- triacyl cyanurate, e.g. triacetyl cyanurate or tribenzoyl cyanurate;
- carboxylic anhydrides, e.g. benzoic anhydride, m-chlorobenzoic anhydride or phthalic anhydride;
- 1,3-diacyl-4,5-diacyloxyimidazolines, e.g. 1,3-diacetyl-4,5-diacetoxyimidazoline;
- tetraacetylglycoluril and tetrapropionylglycoluril;
- diacylated 2,5-diketopiperazines, e.g. 1,4-diacetyl-2,5-diketopiperazine;
- acylation products of propylenediurea and 2,2,-di-methylpropylenediurea, e.g. tetraacetylpropylene-diurea;
- α-acyloxypolyacylmalonamides, e.g. α-acetoxy-N,N'-diacetylmalonamide;
- diacyldioxohexahydro-1,3,5-triazines, e.g. 1,5-diacetyl-2,4-dioxohexahydro-1,3,5-triazine.

It is likewise possible to use 1-alkyl- or 1-aryl-(4H)-3,1-benzoxazin-4-ones, as are described, for example, in EP-B1-0 332 294 and EP-B 0 502 013. In particular, it is possible to use 2-phenyl-(4H)-3,1-benzoxazin-4-one and 2-methyl-(4H)-3,1-benzoxazin-4-one.

It is also possible to use cationic nitriles, as described, for example, in EP 303 520 and EP 458 391 A1. Examples of suitable cationic nitriles are the methosulfates or tosylates of trimethylammoniumacetonitrile, N,N-dimethyl-N-octylammoniumacetonitrile, 2-(trimethylammonium)propio-nitrile, 2-(trimethylammonium)-2-methylpropionitrile, N-methylpiperazinium-N,N'-diacetonitrile and N-methylmorpholiniumacetonitrile.

Particularly suitable crystalline bleach activators are tetraacetylethylenediamine (TAED), NOBS, isoNOBS, carbonylbiscaprolactam, benzoylcaprolactam, bis(2-propylimino) carbonate, bis(cyclohexylimino) carbonate, O-benzoylacetone oxime and 1-phenyl-(4H)-3,1-benzoxazin-4-one, anthranil, phenylanthranil, N-methylmorpholinoacetonitrile, N-octanoylcaprolactam (OCL) and N-methylpiperazine-N,N'-diacetonitrile, and liquid or poorly crystallizing bleach activators in a form formulated as a solid product.

Bleach Stabilizer

These are additives which are able to adsorb, bind or complex traces of heavy metal. Examples of additives with a bleach-stabilizing action which can be used according to the invention are polyanionic compounds, such as polyphosphates, polycarboxylates, polyhydroxy-polycarboxylates, soluble silicates in the form of completely or partially neutralized alkali metal or alkaline earth metal salts, in particular in the form of neutral Na or Mg salts, which are relatively weak bleach stabilizers. Strong bleach stabilizers which can be used according to the invention are, for example, complexing agents, such as ethylenediaminetetraacetate (EDTA), nitrilotriacetic acid (NTA), methylglycine-diacetic acid (MGDA), β-alaninediacetic acid (ADA), ethylenediamine-N,N'-disuccinate (EDDS) and phosphonates, such as ethylenediaminetetramethylene-phosphonate, diethylenetriaminepentamethylene-phosphonate or hydroxyethylidene-1,1-diphosphonic acid in the form of the acids or as partially or completely neutralized alkali metal salts. The complexing agents are preferably used in the form of their Na salts.

The detergents according to the invention preferably comprise at least one bleach stabilizer, particularly preferably at least one of the abovementioned strong bleach stabilizers.

In the field of textile washing, bleaching and household cleaning and in the commercial sector, the bleach or textile detergent compositions described may, in accordance with one embodiment of the invention, comprise virtually all customary constituents of detergents, bleaches and cleaners. In this way, it is possible, for example, to formulate compositions which are specifically suitable for textile treatment at low temperatures, and also those which are suitable in a number of temperature ranges up to and including the traditional range of the boil wash.

In addition to bleach compositions, the main constituents of textile detergents and cleaners are builders, i.e. inorganic builders and/or organic cobuilders, and surfactants, in particular anionic and/or nonionic surfactants. In addition, it is also possible for other customary auxiliaries and adjuncts, such as extenders, complexing agents, phosphonates, dyes, corrosion inhibitors, antiredeposition agents and/or soil release polymers, color-transfer inhibitors, bleach catalysts, peroxide stabilizers, electrolytes, optical brighteners, enzymes, perfume oils, foam regulators and activating substances, to be present in these compositions if this is advantageous.

Inorganic Builders (Builder Substances)

Suitable inorganic builder substances are all customary inorganic builders, such as aluminosilicates, silicates, carbonates and phosphates.

Examples of suitable inorganic builders are aluminosilicates having ion-exchanging properties, such as, for example, zeolites. Various types of zeolites are suitable, in particular zeolite A, X, B, P, MAP and HS in their Na form or in forms in which Na has partially been replaced by other cations such Li, K, Ca, Mg or ammonium. Suitable zeolites are described, for example, in EP-A 038 591, EP-A 021 491, EP-A 087 035, U.S. Pat. No. 4,604,224, GB-A2 013 259, EP-A 522 726, EP-A 384 070 and WO-A 94/24 251.

Further suitable inorganic builders are, for example, amorphous or crystalline silicates, such as, for example, amorphous disilicates, crystalline disilicates, such as the phyllosilicate SKS-6 (manufacturer: Hoechst). The silicates can be used in the form of their alkali metal, alkaline earth metal or ammonium salts. Preference is given to using Na, Li and Mg silicates.

Anionic Surfactants

Suitable anionic surfactants are the linear and/or slightly branched alkylbenzenesulfonates (LAS) according to the invention.

Further suitable anionic surfactants are, for example, fatty alcohol sulfates of fatty alcohols having 8 to 22, preferably 10 to 18, carbon atoms, e.g. $C_9$- to $C_{11}$-alcohol sulfates, $C_{12}$- to $C_{13}$-alcohol sulfates, cetyl sulfate, myristyl sulfate, palmityl sulfate, stearyl sulfate and tallow fatty alcohol sulfate.

Further suitable anionic surfactants are sulfated ethoxylated $C_8$- to $C_{22}$-alcohols (alkyl ether sulfates) or soluble salts thereof. Compounds of this type are prepared, for example, by firstly alkoxylating a $C_8$- to $C_{22}$-alcohol, preferably a $C_{10}$–$C_{18}$ alcohol, e.g. a fatty alcohol, and then sulfating the alkoxylation product. For the alkoxylation, preference is given to using ethylene oxide, in which case 2 to 50 mol, preferably 3 to 20 mol, of ethylene oxide are used per mole of fatty alcohol. The alkoxylation of the alcohols can, however, also be carried out using propylene oxide on its own and optionally butylene oxide. Also suitable are those alkoxylated $C_8$- to $C_{22}$-alcohols which contain ethylene oxide and propylene oxide or ethylene oxide and butylene oxide. The alkoxylated $C_8$ to $C_{22}$-alcohols may contain the ethylene oxide, propylene oxide and butylene oxide units in the form of blocks or in random distribution.

Further suitable anionic surfactants are N-acylsarcosinates having aliphatic saturated or unsaturated $C_8$- to $C_{25}$-acyl radicals, preferably $C_{10}$- to $C_{20}$-acyl radicals, e.g. N-oleoylsarcosinate.

The anionic surfactants are preferably added to the detergent in the form of salts. Suitable cations in these salts are alkali metal salts, such as sodium, potassium and lithium and ammonium salts such as, for example, hydroxyethylammonium, di(hydroxyethyl)ammonium and tri(hydroxyethyl) ammonium salts.

The detergents according to the invention preferably comprise $C_{10}$- to $C_{13}$-linear and/or slightly branched alkylbenzenesulfonates (LAS).

Nonionic Surfactants

Suitable nonionic surfactants are, for example, alkoxylated $C_8$- to $C_{22}$-alcohols, such as fatty alcohol alkoxylates or oxo alcohol alkoxylates. The alkoxylation can be carried out with ethylene oxide, propylene oxide and/or butylene oxide. Surfactants which can be used here are any alkoxylated alcohols which contain at least two molecules of an abovementioned alkylene oxide in added form. Block polymers of ethylene oxide, propylene oxide and/or butylene oxide are also suitable here, or addition products which contain said alkylene oxides in random distribution. Per mole of alcohol, 2 to 50 mol, preferably 3 to 20 mol, of at least one alkylene oxide are used. The alkylene oxide used is preferably ethylene oxide. The alcohols preferably have 10 to 18 carbon atoms.

A further class of suitable nonionic surfactants are alkylphenol ethoxylates having $C_6$–$C_{14}$-alkyl chains and 5 to 30 mol of ethylene oxide units.

Another class of nonionic surfactants are alkyl polyglucosides having 8 to 22, preferably 10 to 18, carbon atoms in the alkyl chain. These compounds contain at most 1 to 20, preferably 1.1 to 5, glucoside units.

Another class of nonionic surfactants are N-alkyl-glucamides of the structure II or III

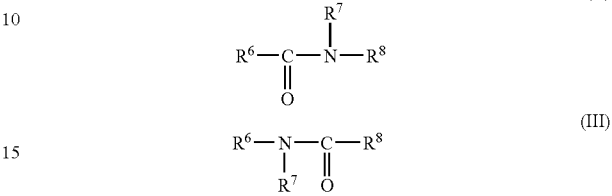

in which $R^6$ is $C_6$- to $C_{22}$-alkyl, $R^7$ is H or $C_1$- to $C_4$-alkyl and $R^8$ is a polyhydroxyalkyl radical having 5 to 12 carbon atoms and at least 3 hydroxyl groups. Preferably, $R^6$ is $C_{10}$- to $C_{18}$-alkyl, $R^7$ is methyl and $R^8$ is a $C_5$- or $C_6$-radical. Such compounds are obtained, for example, by the acylation of reductively aminated sugars with acid chlorides of $C_{10}$–$C_{18}$-carboxylic acids.

The detergents according to the invention preferably comprise $C_{10}$–$C_{16}$-alcohols ethoxylated with 3–12 mol of ethylene oxide, particularly preferably ethoxylated fatty alcohols as nonionic surfactants.

Organic Cobuilders

Examples of suitable low molecular weight polycarboxylates as organic cobuilders are:

$C_4$- to $C_{20}$-di-, -tri- and -tetracarboxylic acids, such as, for example, succinic acid, propanetricarboxylic acid, butanetetracarboxylic acid, cyclopentanetetracarboxylic acid and alkyl- and alkenylsuccinic acids having $C_2$- to $C_{16}$-alkyl or -alkenyl radicals;

$C_4$- to $C_{20}$-hydroxycarboxylic acids, such as, for example, malic acid, tartaric acid, gluconic acid, glucaric acid, citric acid, lactobionic acid and sucrose mono-, -di- and -tricarboxylic acid;

aminopolycarboxylates, such as, for example, nitrilo-triacetic acid, methylglycinediacetic acid, alaninediacetic acid, ethylenediaminetetraacetic acid and serinediacetic acid;

salts of phosphonic acids, such as, for example, hydroxyethanediphosphonic acid, ethylenediaminetetra(methylenephosphonate) and diethylenetriaminepenta(methylenephosphonate).

Examples of suitable oligomeric or polymeric polycarboxylates as organic cobuilders are:

oligomaleic acids, as described, for example, in EP-A-451 508 and EP-A-396 303;

co- and terpolymers of unsaturated $C_4$–$C_8$-dicarboxylic acids, where, as comonomers, monoethylenically unsaturated monomers from group (i) in amounts of up to 95% by weight from group (ii) in amounts of up to 60% by weight from group (iii) in amounts of up to 20% by weight may be present in copolymerized form.

Examples of suitable unsaturated $C_4$–$C_8$-dicarboxylic acids are, for example, maleic acid, fumaric acid, itaconic acid and citraconic acid. Preference is given to maleic acid.

The group (i) includes monoethylenically unsaturated $C_3$–$C_8$-monocarboxylic acids, such as, for example, acrylic acid, methacrylic acid, crotonic acid and vinyl acetic acid. Preference is given to using acrylic acid and methacrylic acid from group (i).

The group (ii) includes monoethylenically unsaturated $C_2$–$C_{22}$-olefins, vinyl alkyl ethers having $C_1$–$C_8$-alkyl groups, styrene, vinyl esters of $C_1$–$C_8$ carboxylic acids, (meth)acrylamide and vinylpyrrolidone. Preference is given to using $C_2$–$C_6$-olefins, vinyl alkyl ethers having $C_1$–$C_4$-alkyl groups, vinyl acetate and vinyl propionate from group (ii).

The group (iii) includes (meth)acrylic esters of $C_1$–$C_8$-alcohols, (meth)acrylonitrile, (meth)acrylamides of $C_1$–$C_8$-amines, N-vinylformamide and vinylimidazole.

If the polymers of group (ii) contain vinyl esters in copolymerized form, these may also be present partly or completely in hydrolyzed form to give vinyl alcohol structural units. Suitable co- and terpolymers are known, for example, from U.S. Pat. No. 3,887,806 and DE-A 43 13 909.

As copolymers of dicarboxylic acids, suitable organic cobuilders are preferably:

copolymers of maleic acid and acrylic acid in the weight ratio 10:90 to 95:5, particularly preferably those in the weight ratio 30:70 to 90:10 having molar masses of from 10 000 to 150 000;

terpolymers of maleic acid, acrylic acid and a vinyl ester of a $C_1$–$C_3$-carboxylic acid in the weight ratio 10(maleic acid):90(acrylic acid+vinyl ester) to 95(maleic acid):5 (acrylic acid+vinyl ester), where the weight ratio of acrylic acid to vinyl ester can vary in the range from 20:80 to 80:20, and particularly preferably terpolymers of maleic acid, acrylic acid and vinyl acetate or vinyl propionate in the weight ratio 20 (maleic acid):80 (acrylic acid+vinyl ester) to 90(maleic acid):10(acrylic acid+vinyl ester), where the weight ratio of acrylic acid to the vinyl ester can vary in the range from 30:70 to 70:30;

copolymers of maleic acid with $C_2$–$C_8$-olefins in the molar ratio 40:60 to 80:20, where copolymers of maleic acid with ethylene, propylene or isobutane in the molar ratio 50:50 are particularly preferred.

Graft polymers of unsaturated carboxylic acids to low molecular weight carbohydrates or hydrogenated carbohydrates, cf. U.S. Pat. No. 5,227,446, DE-A-44 15 623, DE-A-43 13 909, are likewise suitable as organic cobuilders.

Examples of suitable unsaturated carboxylic acids in this connection are maleic acid, fumaric acid, itaconic acid, citraconic acid, acrylic acid, methacrylic acid, crotonic acid and vinyl acetic acid, and mixtures of acrylic acid and maleic acid which are grafted on in amounts of from 40 to 95% by weight, based on the component to be grafted.

For the modification, it is additionally possible for up to 30% by weight, based on the component to be grafted, of further monoethylenically unsaturated monomers to be present in copolymerized form. Suitable modifying monomers are the abovementioned monomers of groups (ii) and (iii).

Suitable graft bases are degraded polysaccharides, such as, for example, acidic or enzymatically degraded starches, inulins or cellulose, reduced (hydrogenated or reductively aminated) degraded polysaccharides, such as, for example, mannitol, sorbitol, aminosorbitol and glucamine, and also polyalkylene glycols having molar masses up to $M_w$=5 000, such as, for example, polyethylene glycols, ethylene oxide/propylene oxide or ethylene oxide/butylene oxide block copolymers, random ethylene oxide/propylene oxide or ethylene oxide/butylene oxide copolymers, alkoxylated mono- or polybasic $C_1$–$C_{22}$-alcohols, cf. U.S. Pat. No. 4,746,456.

From this group, preference is given to using grafted degraded or degraded reduced starches and grafted polyethylene oxides, in which case 20 to 80% by weight of monomers, based on the graft component, are used in the graft polymerization. For the grafting, preference is given to using a mixture of maleic acid and acrylic acid in the weight ratio from 90:10 to 10:90.

Polyglyoxylic acids as organic cobuilders are described, for example, in EP-B-001 004, U.S. Pat. No. 5,399,286, DE-A-41 06 355 and EP-A-656 914. The end-groups of the polyglyoxylic acids may have different structures.

Polyamidocarboxylic acids and modified polyamidocarboxylic acids as organic cobuilders are known, for example, from EP-A-454 126, EP-B-511 037, WO-A 94/01486 and EP-A-581 452.

As organic cobuilders, preference is also given to using polyaspartic acid or cocondensates of aspartic acid with further amino acids, $C_4$–$C_{25}$-mono- or -dicarboxylic acids and/or $C_4$–$C_{25}$-mono- or -diamines. Particular preference is given to using polyaspartic acids prepared in phosphorus-containing acids and modified with $C_6$–$C_{22}$-mono- or -dicarboxylic acids or with $C_6$–$C_{22}$-mono- or -diamines.

Condensation products of citric acid with hydroxycarboxylic acids or polyhydroxy compounds as organic cobuilders are known, for example, from WO-A 93/22362 and WO-A 92/16493. Such carboxyl-containing condensates usually have molar masses up to 10 000, preferably up to 5 000.

Antiredeposition Agents and Soil Release Polymers

Suitable soil release polymers and/or antiredeposition agents for detergents are, for example:

polyesters of polyethylene oxides with ethylene glycol and/or propylene glycol and aromatic dicarboxylic acids or aromatic and aliphatic dicarboxylic acids;

polyesters of polyethylene oxides terminally capped at one end with di- and/or polyhydric alcohols and dicarboxylic acid.

Such polyesters are known, for example from U.S. Pat. No. 3,557,039, GB-A 1 154 730, EP-A-185 427, EP-A-241 984, EP-A-241 985, EP-A-272 033 and U.S. Pat. No. 5,142,020.

Further suitable soil release polymers are amphiphilic graft or copolymers of vinyl and/or acrylic esters on polyalkylene oxides (cf. U.S. Pat. No. 4,746,456, U.S. Pat. No. 4,846,995, DE-A-37 11 299, U.S. Pat. No. 4,904,408, U.S. Pat. No. 4,846,994 and U.S. Pat. No. 4,849,126) or modified celluloses, such as, for example, methylcellulose, hydroxypropylcellulose or carboxymethylcellulose.

Color-transfer Inhibitors

Examples of the color-transfer inhibitors used are homo- and copolymers of vinylpyrrolidone, vinylimidazole, vinyloxazolidone and 4-vinylpyridine N-oxide having molar masses of from 15 000 to 100 000, and crosslinked finely divided polymers based on these monomers. The use mentioned here of such polymers is known, cf. DE-B-22 32 353, DE-A-28 14 287, DE-A-28 14 329 and DE-A-43 16 023.

Enzymes

Suitable enzymes are, for example, proteases, amylases, lipases and cellulases, in particular proteases. It is possible to use two or more enzymes in combination.

In addition to use in detergents and cleaners for the domestic washing of textiles, the detergent compositions which can be used according to the invention can also be used in the sector of commercial textile washing and of commercial cleaning. In this field of use, peracetic acid is usually used as bleach, which is added to the wash liquor as an aqueous solution.

Use in Textile Detergents

A typical pulverulent or granular heavy-duty detergent according to the invention may, for example, have the following composition:

- 0.5 to 50% by weight, preferably 5 to 30% by weight, of at least one anionic and/or nonionic surfactant,
- 0.5 to 60% by weight, preferably 15 to 40% by weight, of at least one inorganic builder,
- 0 to 20% by weight, preferably 0.5 to 8% by weight, of at least one organic cobuilder,
- 2 to 35% by weight, preferably 5 to 30% by weight, of an inorganic bleach,
- 0.1 to 20% by weight, preferably 0.5 to 10% by weight, of a bleach activator, optionally in a mixture with further bleach activators,
- 0 to 1% by weight, preferably up to at most 0.5% by weight, of a bleach catalyst,
- 0 to 5% by weight, preferably 0 to 2.5% by weight, of a polymeric color-transfer inhibitor,
- 0 to 1.5% by weight, preferably 0.1 to 1.0% by weight, of protease,
- 0 to 1.5% by weight, preferably 0.1 to 1.0% by weight, of lipase,
- 0 to 1.5% by weight, preferably 0.2 to 1.0% by weight, of a soil release polymer, ad 100% with customary auxiliaries and adjuncts and water.

Inorganic builders preferably used in detergents are sodium carbonate, sodium hydrogen carbonate, zeolite A and P, and amorphous and crystalline Na silicates.

Organic cobuilders preferably used in detergents are acrylic acid/maleic copolymers, acrylic acid/maleic acid/vinyl ester terpolymers and citric acid.

Inorganic bleaches preferably used in detergents are sodium perborate and sodium carbonate perhydrate.

Anionic surfactants preferably used in detergents are the novel linear and slightly branched alkylbenzenesulfonates (LAS), fatty alcohol sulfates and soaps. Nonionic surfactants preferably used in detergents are $C_{11}$–$C_{17}$-oxo alcohol ethoxylates having 3–13 ethylene oxide units, $C_{10}$–$C_{16}$-fatty alcohol ethoxylates having 3–13 ethylene oxide units, and ethoxylated fatty alcohols or oxo alcohols additionally alkoxylated with 1–4 propylene oxide or butylene oxide units.

Enzymes preferably used in detergents are protease, lipase and cellulase. Of the commercially available enzymes, amounts of from 0.05 to 2.0% by weight, preferably 0.2 to 1.5% by weight, of the formulated enzyme, are generally added to the detergent. Suitable proteases are, for example, Savinase, Desazym and Esperase (manufacturer: Novo Nordisk). A suitable lipase is, for example, Lipolase (manufacturer: Novo Nordisk). A suitable cellulase is, for example, Celluzym (manufacturer: Novo Nordisk).

Soil release polymers and antiredeposition agents preferably used in detergents are graft polymers of vinyl acetate on polyethylene oxide of molecular mass 2 500–8 000 in the weight ratio 1.2:1 to 3.0:1, polyethylene terephthalates/oxyethylene terephthalates of molar mass 3 000 to 25 000 from polyethylene oxides of molar mass 750 to 5 000 with terephthalic acid and ethylene oxide and a molar ratio of polyethylene terephthalate to polyoxyethylene terephthalate of from 8:1 to 1:1, and block polycondensates according to DE-A-44 03 866.

Color-transfer inhibitors preferably used in detergents are soluble vinylpyrrolidone and vinylimidazole copolymers having molar masses greater than 25 000, and finely divided crosslinked polymers based on vinylimidazole.

The pulverulent or granular detergents according to the invention can comprise up to 60% by weight of inorganic extenders. Sodium sulfate is usually used for this purpose. However, the detergents according to the invention preferably have a low content of extenders and comprise only up to 20% by weight, particularly preferably only up to 8% by weight, of extenders.

The detergents according to the invention can have various bulk densities in the range from 300 to 1 200 g/l, in particular 500 to 950 g/l. Modem compact detergents generally have high bulk densities and exhibit a granular structure.

The invention is described in more detail by reference to the examples below.

EXAMPLE 1

A butadiene-free $C_4$ fraction with a total butene content of 84.2% by weight and a 1-butene to 2-butene molar ratio of 1 to 1.06 is passed continuously at 40° C. and 10 bar over a tubular reactor fitted with $Re_2O_7/Al_2O_3$ heterogeneous catalyst. The space velocity in the example is 4 500 kg/m² h. The reaction discharge is separated by distillation and comprises the following components (data in percent by mass):

ethene 1.15%; propene 18.9%, butanes 15.8%, 2-butenes 19.7%, 1-butene 13.3%, i-butene 1.0%, 2-pentene 19.4%, methylbutene 0.45%, 3-hexene 10.3%.

2-Pentene and 3-hexene are isolated from the product by distillation in purities of >99% by weight.

EXAMPLE 2

Continuous Dimerization of 3-hexene in the Fixed-bed Process

| Catalyst: | 50% NiO, 34% $SiO_2$, 13% $TiO_2$, 3% $Al_2O_3$ (as in DE 43 39 713) used as 1–1.5 mm chips (100 ml), conditioned for 24 h at 160° C. in $N_2$ |
|---|---|
| Reactor: | isothermal, 16 mm Ø reactor |
| WHSV: | 0.25 kg/l.h |
| Pressure: | 20 to 25 bar |
| Temperature: | 100 to 160° C. |

| Temperature (° C.) | Feed stock | 100 | 120 | 140 | 160 | 160 | Collective product | $C_{12}$ distillate |
|---|---|---|---|---|---|---|---|---|
| Pressure (bar) | | 20 | 20 | 20 | 25 | 25 | — | |

-continued

| | | | | | | | | |
|---|---|---|---|---|---|---|---|---|
| Operating hours | | 12 | 19 | 36 | 60 | 107 | | |
| Liquid produced (g/h) | | 24 | 27 | 27 | 28 | 27 | | |
| Composition (% by weight) | | | | | | | | |
| $C_6$ | 99.9 | 68.5 | 52.7 | 43.6 | 57.0 | 73.2 | n.d. | 0.1 |
| $C_7$–$C_{11}$ | 0.1 | 0.2 | 0.2 | 0.3 | 0.2 | 0.2 | | — |
| $C_{12}$ | | 25.9 | 38.6 | 44.0 | 35.6 | 23.6 | | 99.9 |
| $C_{13}+$ | | 5.4 | 8.5 | 12.1 | 7.2 | 3.0 | | — |
| Conversion | | 31.4 | 47.2 | 56.4 | 42.9 | 26.7 | | |
| C12 selectivity (% by weight) | | 82.5 | 81.8 | 78.2 | 83.0 | 88.4 | | |
| S content in the liquid produced (ppm) | <1 | n.d. | n.d. | n.d. | n.d. | n.d. | n.d. | n.d. |

The collective product was distilled to a $C_{12}$ purity of 99.9% by weight.

EXAMPLE 3

2-Pentene from the raffinate II metathesis was dimerized continuously as in example 2 over an Ni heterogeneous catalyst. Fractional distillation of the product gave a decene fraction with a purity of 99.5%.

EXAMPLE 4

A mixture of 2-pentene and 3-hexene from the raffinate II methathesis was dimerized as in example 2 and example 3. Fractional distillation of the product gave a decene/undecene/dodecene fraction with a purity of 99.5%

EXAMPLE 5

The $C_{12}$-olefin fraction from example 2 is alkylated with benzene in the molar ratio 1:10. For this, the reaction mixture is introduced into an autoclave (300 ml) which is equipped with a stirrer and a catalyst basket. 25% by weight, based on the mass of the olefin, of zeolite mordenith catalyst (MOR) are introduced into the catalyst basket. The autoclave is sealed and flushed twice with nitrogen ($N_2$). The autoclave is then heated to 180° C. The reaction mixture is then reacted for 12 h, then cooled, any catalyst particles are filtered from the reaction mixture, and the reaction mixture is analyzed by means of gas chromatography-mass spectrometry coupling. Excess benzene and low-boiling components are distilled off, and the alkylaryl mixture obtained is analyzed by means of gas chromatography-mass spectrometry coupling and $C^{13}$-NMR.

EXAMPLE 6

A 2 l four-necked flask fitted with magnetic stirrer, thermometer, dropping funnel, gas inlet frit and gas outlet is charged with 1 900 g of $SO_3$-depleted oleum. This flask is connected via the gas outlet to a 1 l three-necked flask via a Viton hose. This 1 l flask fitted with paddle stirrer, thermometer, gas inlet frit and gas outlet is charged with the alkylbenzene mixture from example 5.

The depleted oleum is brought to 120° C. in the $SO_3$-developer, and the oleum (65% strength) is added via a dropping funnel over the course of 30 minutes. Using a stream of nitrogen of 80 l/h, the $SO_3$ gas is stripped out and passed into the alkylbenzene via a 6 mm inlet tube. The temperature of the alkylbenzene/alkylbenzenesulfonic acid mixture increases slowly to 40° C. and is maintained at 40° C. using cooling water. The residual gas is removed by suction using a water-jet pump.

The molar ratio of $SO_3$/alkylbenzene is 1.01:1.

After a postreaction time of 4 h, the alkylbenzene-sulfonic acid formed is stabilized with 0.4% by weight of water and then neutralized with NaOH to give the alkylbenzenesulfonate.

EXAMPLE 7

A mixture of the $C_{10}$-/$C_{11}$-/$C_{12}$-olefin fractions from example 4 is alkylated with benzene in the molar ratio 1:10. For this, the reaction mixture is introduced into an autoclave (300 ml) which is provided with a stirrer and a catalyst basket. 25% by weight, based on the mass of the olefin, of zeolite mordenite catalyst (MOR) are introduced into the catalyst basket. The autoclave is sealed and flushed twice with nitrogen ($N_2$). The autoclave is then heated to 200° C. The reaction mixture is reacted for 12 h, then cooled, any catalyst particles are filtered from the reaction mixture, and the reaction mixture is analyzed by means of gas chromatography-mass spectrometry coupling.

Excess benzene and low-boiling fractions are distilled off, and the alkylaryl mixture obtained is analyzed by means of gas chromatography-mass spectrometry coupling and $C^{13}$-NMR.

EXAMPLE 8

The alkylbenzene mixture from example 7 is converted to the alkylbenzenesulfonate analogously to the description in example 6.

EXAMPLE 9

A mixture of the $C_{10}$-/$C_{11}$-/$C_{12}$-olefin fractions from example 4 is alkylated with benzene in the molar ratio 1:2. For this, the reaction mixture is introduced into an autoclave (300 ml) which is provided with a stirrer and a catalyst basket. 5% by weight, based on the mass of the olefin, of zeolite ZSM-12 catalyst are introduced into the catalyst basket. The autoclave is sealed and flushed twice with nitrogen ($N_2$). The autoclave is then heated to 180° C. The reaction mixture is reacted for 12 h, then cooled, any catalyst particles are filtered from the reaction mixture, and the reaction mixture is analyzed by means of gas chromatography-mass spectrometry coupling.

Excess benzene and low-boiling fractions are distilled off, and the alkylaryl mixture obtained is analyzed by means of gas chromatography-mass spectrometry coupling and $C^{13}$-NMR.

EXAMPLE 10

The alkylbenzene mixture from example 9 is converted to the alkylbenzenesulfonate analogously to the description in example 6.

EXAMPLE 11

A $C_{12}$-olefin fraction from example 2 is alkylated with benzene in the molar ratio 1:4. For this, the reaction mixture is introduced into an autoclave (300 ml) which is provided with a stirrer and a catalyst basket. 10% by weight, based on the mass of the olefin, of zeolite beta (BEA) catalyst are introduced into the catalyst basket. The autoclave is sealed and flushed twice with nitrogen ($N_2$). The autoclave is then heated to 180° C. The reaction mixture is reacted for 12 h, then cooled, any catalyst particles are filtered from the reaction mixture, and the reaction mixture is analyzed by means of gas chromatography-mass spectrometry coupling.

Excess benzene and low-boiling fractions are distilled off, and the resulting alkylaryl mixture is analyzed by means of gas chromatography-mass spectrometry coupling and $C^{13}$-NMR.

EXAMPLE 12

The alkylbenzene mixture from example 11 is converted to the alkylbenzenesulfonate analogously to the description in example 6.

EXAMPLE 13

A mixture of the $C_{10}$-/$C_{11}$-/$C_{12}$-olefin fractions from example 4 is alkylated with benzene in the molar ratio 1:4. For this, the reaction mixture is introduced into an autoclave (300 ml) which is provided with a stirrer and a catalyst basket. 10% by weight, based on the mass of the olefin, of zeolite MCM-22 catalyst are introduced into the catalyst basket. The autoclave is sealed and flushed twice with nitrogen ($N_2$). The autoclave is then heated to 200° C. The reaction mixture is reacted for 12 h, then cooled, any catalyst particles are filtered from the reaction mixture, and the reaction mixture is analyzed by means of gas chromatography-mass spectrometry coupling.

Excess benzene and low-boiling fractions are distilled off, and the resulting alkylaryl mixture is analyzed by means of gas chromatography-mass spectrometry coupling and $C^{13}$-NMR.

EXAMPLE 14

1 l/h of oleum (65%) in concentrated sulfuric acid is introduced into a heated (120° C.) 10 l four-necked flask using a pump. 130 l/h of dry air are passed through the sulfuric acid via a frit; this air strips out the $SO_3$. The $SO_3$-enriched stream of air (about 4% of $SO_3$) is brought into contact with an alkylbenzene mixture from example 13 in a 2 m-long falling-film reactor, at approximately 40–50° C. (10–15° C. double-jacket water cooling), and sulfonates this mixture. The molar ratio of $SO_3$/alkylbenzene is 1.01:1. The reaction time in the falling-film reactor is approximately 10 sec. The product is pumped to an afterripening container where it remains for approximately 4–8 h. The sulfonic acid is then stabilized with 0.4% by weight of water and neutralized with NaOH to give the alkylbenzenesulfonate.

EXAMPLE 15

A $C_{12}$-olefin fraction from example 2 is alkylated with benzene in the molar ratio 1:10. Thus, the reaction mixture is introduced into a four-necked flask (2 l), which is provided with a stirrer, a thermometer, a reflux condenser with a gas offtake and a dropping funnel. The flask is charged with benzene and $AlCl_3$, the temperature is increased to 80° C., and the olefin mixture is metered in slowly. The reaction mixture is afterreacted for ½ h, then cooled, any catalyst particles are filtered from the reaction mixture, and the reaction mixture is neutralized with NaOH. Washing with water is then carried out, and the product is dried.

Excess benzene and low-boiling fractions are distilled off, and the resulting alkylaryl mixture is analyzed by means of gas chromatography-mass spectrometry coupling and $C^{13}$-NMR.

EXAMPLE 16

The alkylbenzene mixture from example 15 is converted to the alkylbenzenesulfonate analogously to the description in example 6.

We claim:

1. A process for the preparation of alkylarylsulfonates, comprising:
    a) reacting a $C_4$-olefin mixture over a metathesis catalyst for the preparation of an olefin composition comprising 2-pentene, 3-hexene or mixtures thereof, and optional removal of 2-pentene, 3 hexene, or mixtures thereof,
    b) dimerizing the 2-pentene, 3-hexene or mixtures thereof obtained in stage a) over a dimerization catalyst to give a mixture containing $C_{10-12}$-olefins, and optional removal of the $C_{10-12}$-olefins,
    c) reacting the mixture containing $C_{10-12}$-olefins or optionally a separated $C_{10-12}$ fraction, with an aromatic hydrocarbon in the presence of an alkylating catalyst to form alkylaromatic compounds,
    d) sulfonating the alkylaromatic compounds obtained in stage c), and neutralizing the resultant mixture to give alkylarylsulfonates, and
    wherein, in the $C_{10-12}$-olefins, the proportion of monosubstitution products is in the range from 40 to 75% by weight, and the proportion of double-branched products is in the range from 5 to 25% by weight.

2. The process as claimed in claim 1, wherein the metathesis catalyst in stage a) is selected from compounds of a metal of transition groups VIb, VIIb, or VIII of the Periodic Table of the Elements.

3. The process as claimed in claim 1, wherein, in stage b), a dimerization catalyst is used, which contains at least one element from transition group VIII of the Periodic Table of the Elements, and the catalyst composition and the reaction conditions are chosen, such that a dimer mixture is obtained, which contains less than 10% by weight of compounds which have a structural element of the formula I (vinylidene group)

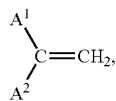 (I)

wherein A¹ and A² are aliphatic hydrocarbon radicals.

4. The process as claimed in claim 1, wherein the olefins obtained in stage b), have a proportion of unbranched olefins of less than 25% by weight.

5. The process as claimed in claim 1, wherein at least 80% of the olefins obtained in stage b), have one branch, or two branches on adjacent carbon atoms, in the range from ¼ to ¾ of the number of carbon atoms in the main chain of the molecule.

6. The process as claimed in claim 1, wherein, in stage c), the alkylating catalyst that is used, leads to alkylaromatic compounds which have an alkyl group that has 1 to 3 carbon atoms with an H/C index of 1, wherein the H/C index defines the number of protons per carbon atom in the alkyl group.

7. The process as claimed in claim 1, wherein at least 80% of the olefins obtained in stage b), have one branch, or two branches on adjacent carbon atoms, in the range from ⅓ to ⅔ of the number of carbon atoms in the main chain of the molecule.

* * * * *